(12) United States Patent
Chen

(10) Patent No.: US 8,521,535 B2
(45) Date of Patent: Aug. 27, 2013

(54) BIOCHEMICAL ANALYZER HAVING MICROPROCESSING APPARATUS WITH EXPANDABLE VOICE CAPACITY

(76) Inventor: Chun-Yu Chen, Taipei (TW)

(*) Notice: Subject to any disclaimer, the term of this patent is extended or adjusted under 35 U.S.C. 154(b) by 470 days.

(21) Appl. No.: 12/943,005

(22) Filed: Nov. 10, 2010

(65) Prior Publication Data

US 2012/0116775 A1    May 10, 2012

(51) Int. Cl.
*G10L 21/00*    (2006.01)

(52) U.S. Cl.
USPC ........ 704/270.1; 704/270; 704/272; 704/260; 704/258; 704/278

(58) Field of Classification Search
USPC ............... 704/270.1, 270, 272, 260, 258, 278
See application file for complete search history.

(56) References Cited

U.S. PATENT DOCUMENTS

| | | | |
|---|---|---|---|
| 2009/0177495 A1* | 7/2009 | Abousy et al. | 705/3 |
| 2010/0121156 A1* | 5/2010 | Yoo | 600/300 |
| 2011/0015504 A1* | 1/2011 | Yoo | 600/301 |
| 2012/0109688 A1* | 5/2012 | Yoo | 705/3 |

\* cited by examiner

*Primary Examiner* — Qi Han

(57) ABSTRACT

A biochemical analyzer having a microprocessing apparatus with expandable voice capacity is characterized in that a driving module is installed in a data processor and a voice carrier is replaceable. Thereby, increase or decrease of voice files can be easily done by replacing the current voice carrier with an alternative voice carrier storing desired voice files, without the need of replacing the driving module together with the voice carrier, thereby saving costs and reducing processing procedures.

5 Claims, 2 Drawing Sheets

BIOCHEMICAL ANALYZER HAVING MICROPROCESSING APPARATUS WITH EXPANDABLE VOICE CAPACITY

BACKGROUND OF THE INVENTION

1. Technical Field

The present invention relates to a biochemical analyzer having a microprocessing apparatus with expandable voice capacity. More particularly, the biochemical analyzer is allowed to be replaceably equipped with voice ICs of different levels of capacity.

2. Description of Related Art

Portable biochemical analyzers are widely used by various chronic patients, for allowing the patients to determine the concentration of certain substances in their body liquid, such as blood, so as to monitor their physical conditions on the go. In view that chronic patients are mostly the elder, a conventional biochemical analyzer may have, in addition to a screen for visually exhibit measured data, a voice function that automatically plays operation reminders, measured data and/or audio warning messages, so as to guide the aged users to use the biochemical analyzer more correctly and effectively. In a currently commercially available biochemical analyzer, it is typical that voice files and the software for driving the voice files are previously burned in separate chips that are then installed on a circuit board in the biochemical analyzer. However, since the voice files recorded in the chip are of particular one or more languages, once the market demands voice files of different languages or other languages, the whole chip has to be disposed and a new chip carrying new voice files has to be made. This not only requires additional cost for making the new chip, but also takes additional time for editing and recording new voice files.

Hence, the aforementioned problems are those to be solved by people skilled in the art.

SUMMARY OF THE INVENTION

In view of the shortcomings of the existing devices, the inventor of the present invention proposes a biochemical analyzer with replaceable voice ICs of different levels of capacity. The objectives of the present invention are listed below.

The first objective of the present invention is to provide the biochemical analyzer, wherein a driving module is installed in a data processor but not a separate element, so as to reduce the number of components and thereby meet the needs of saving manufacturing costs and advocating environmental protection, and wherein a voice carrier is independently detachable and replaceable by other voice carriers that have different levels of capacity and store required voice files, so as to realize functional expansion of the biochemical analyzer.

The second objective of the present invention is to provide the biochemical analyzer, wherein the data processor further comprises a signal amplifying module, which serves to amplify audio signals of the voice files stored in the voice carrier for the voice player to play.

BRIEF DESCRIPTION OF THE DRAWINGS

The invention as well as a preferred mode of use, further objectives and advantages thereof will be best understood by reference to the following detailed description of an illustrative embodiment when read in conjunction with the accompanying drawings, wherein.

DETAILED DESCRIPTION OF THE INVENTION

Figure 1:
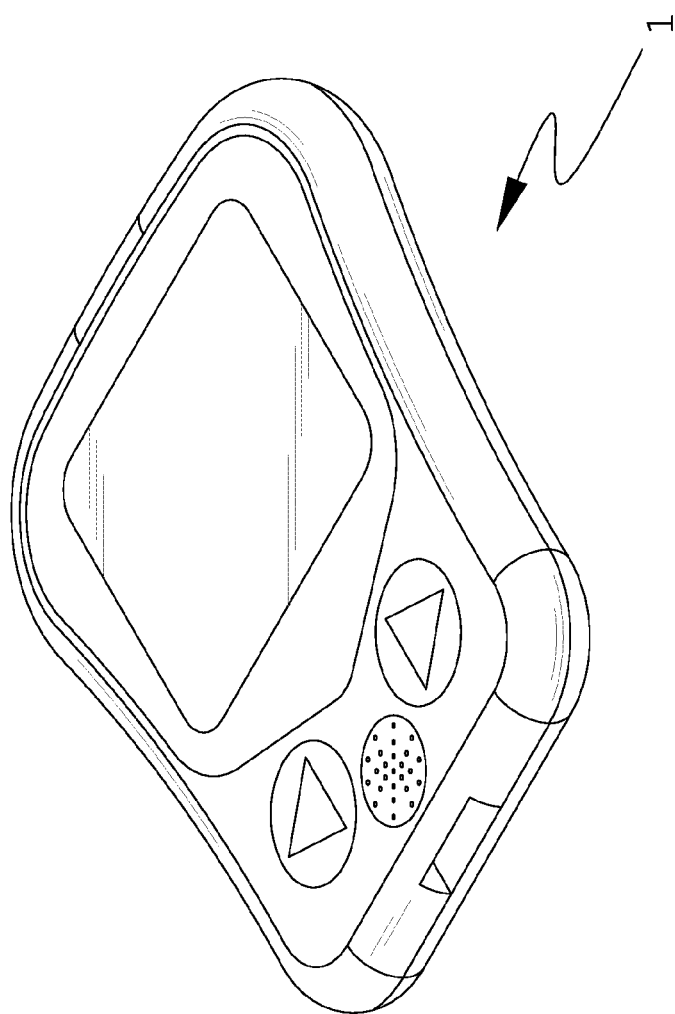
FIG. 1 is a perspective view of the present invention.
Figure 2:
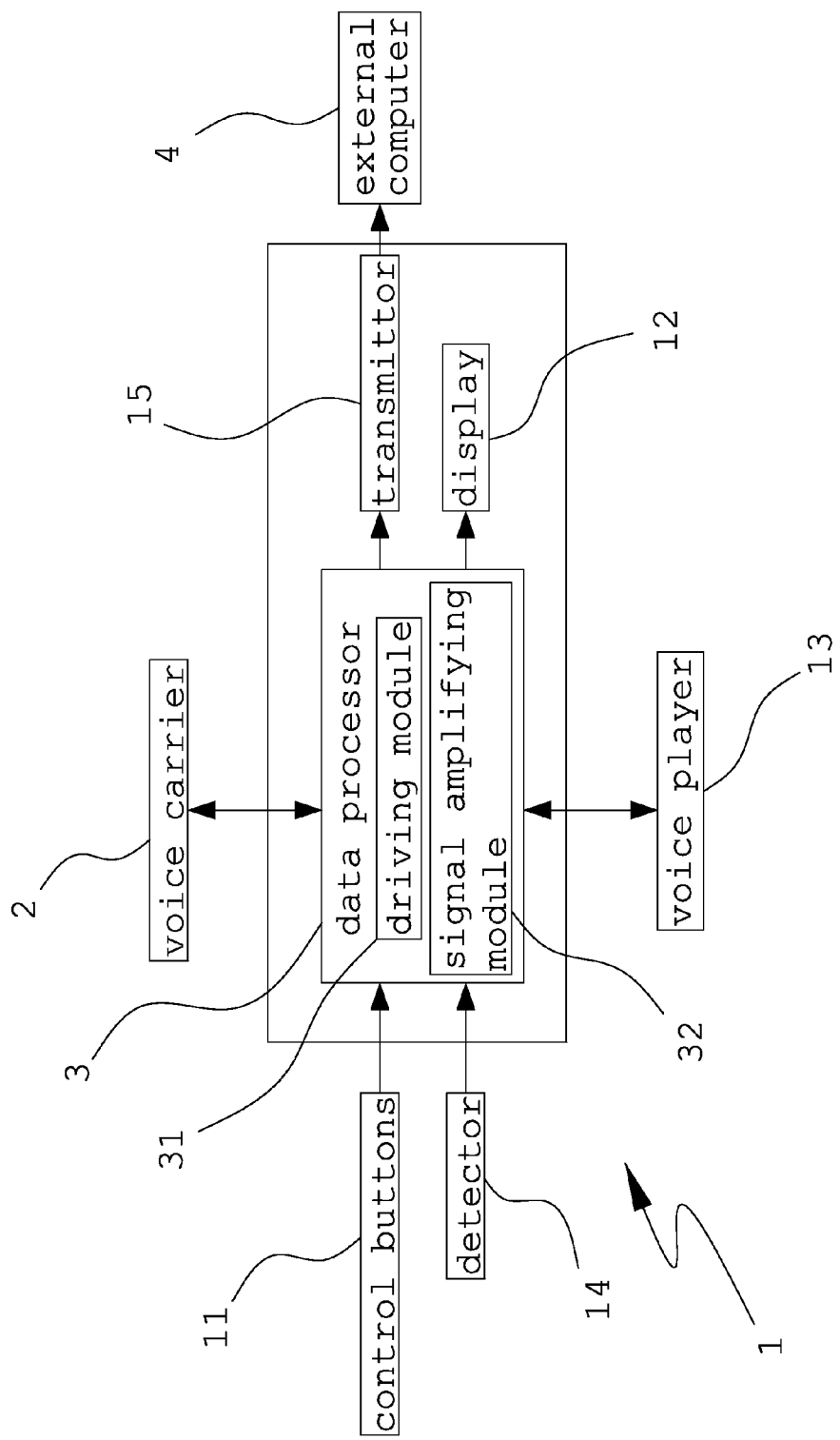
FIG. 2 is a block diagram of the present invention.

First, please refer to FIG. 1 and FIG. 2, for a perspective view and a block diagram of the present invention. As particularly shown in the drawings, a biochemical analyzer 1 comprises:
 a display 12 being configured to display information and data related to the biochemical analyzer 1,
 a voice player 13 being configured to play voice;
 a detector 14 being configured to conduct assays;
 a voice carrier 2 storing voice files and being replaceable;
 a data processor 3 being configured to process and store assay results of the assays coming from the detector 14;
 a driving module 31 being preset in the data processor 3 and configured to drive the voice player 13 to play the voice files stored in the voice carrier 2; and
 a signal amplifying module 32 being preset in the data processor 3.

In use of the biochemical analyzer 1, a test strip moistened with, for example, blood, is placed in the detector 14 at one side of the biochemical analyzer 1 for the detector 14 to analyze the blood on the test strip. The assay results about the blood derived from the detector 14 are then processed and stored by the data processor 3. In addition to one or more control buttons 11 to be operated to control and set functions of the biochemical analyzer 1, and the display 12 presenting a user with measured data, the biochemical analyzer 1 has a voice player 13. The data processor 3 stores the processed data, and the driving module 31 drives the voice files stored in the voice carrier 2, so that the voice player 13 can play particular said voice files according to a user's previous setting, thereby allowing the user to learn the assay results not only through the visual message shown in the display 12 but also through the audio message played by the voice player 13. Moreover, the biochemical analyzer 1 has a transmitter 15 that supports wired and wireless transmission, by which the user is allowed to transmit the assay results to an external computer 4 in a wired or wireless manner. The data processor 3 further comprises a signal amplifying module 32, which serves to stably amplify the audio signals of the voice files stored in the voice carrier 2 for the voice player 13 to display the corresponding audio message. While being explained with the above example of blood assay for glucose, the biochemical analyzer 1 of the present invention may be one serving to monitor human blood pressure, heartbeat or other physical conditions, without limitation.

Since the conventional biochemical analyzer usually has its voice files and software for driving the voice files in separate chips, it needs at least two chips. Meantime, the chips are typically pre-recorded with voice files of one or more particular languages, so the circuit board of the conventional biochemical analyzer has to be entirely changed if different voice files are required. As a remedy for the problem of the prior art, the present invention specially makes the biochemical analyzer 1 in such a way that the driving module 31 is installed in the data processor 3 but not another chip, so as to save one chip and meet the needs of saving manufacturing costs and advocating environmental protection. In addition, since the voice carrier 2 is replaceable and is a memory capable of recording voice files, such as an ROM (read-only memory), when voice files of different languages are required, the voice carrier 2 can be directly accessed for modification, replacement, deletion or addition of voice files. When it is desired to provide voice files of more languages, which require a voice carrier of higher capacity, the originally equipped voice carrier 2 can be detached from the biochemical analyzer 1 and replaced by another voice carrier 2 of higher capacity, thereby endowing the biochemical analyzer 1 with expandability and meeting various users' changing needs.

The present invention has been described with reference to the preferred embodiments and it is understood that the embodiments are not intended to limit the scope of the present invention. Moreover, as the contents disclosed herein should be readily understood and can be implemented by a person skilled in the art, all equivalent changes or modifications which do not depart from the concept of the present invention should be encompassed by the appended claims.

What is claimed is:

1. A biochemical analyzer having a microprocessing apparatus with expandable voice capacity, the biochemical analyzer comprising:
   a detector being configured to conduct assays;
   a data processor, connected to said detector, comprising a driving module and a signal amplifying module, being configured to process and store assay results of the assays coming from the detector;
   a voice carrier, connected to said data processor, being configured to store voice files and being demountable and replaceable;
   a voice player, connected to said data processor, being configured to play voice files stored in the voice carrier by the driving module and increase the volume of the voice by the signal amplifying module of said data processor;
   a display, connected to said data processor, being configured to display information and data related to the biochemical analyzer;
   a transmitter, connected to the data processor, being configured to transmit the assay results to an external computer;
   thereby the driving module solving the problem of being demountable and replaceable without diver on the voice carrier, needing not to be set separately in an additional element, since the voice carrier is replaceable, other voice carriers of different levels of capacity being allowed to work with the biochemical analyzer for expansibility; and the signal amplifying module serving to stably amplify audio signals of the voice files in the voice carrier for the voice player to play the voice files.

2. The biochemical analyzer of claim 1, wherein the voice carrier contains the voice files of at least one language.

3. The biochemical analyzer of claim 1, wherein the transmitter supports wired transmission.

4. The biochemical analyzer of claim 1, wherein the transmitter supports wireless transmission.

5. The biochemical analyzer of claim 1, wherein the data processor, mounted to a set of control buttons, being configured to input the commands to the voice carrier, voice player, transmitting module and display.

* * * * *